(12) United States Patent
Lee

(10) Patent No.: US 6,898,453 B2
(45) Date of Patent: May 24, 2005

(54) METHOD AND APPARATUS FOR CALCULATING BLOOD FLOW PARAMETERS

(75) Inventor: Ting Y. Lee, London (CA)

(73) Assignee: The John P. Robarts Research Institute, London (CA)

( * ) Notice: Subject to any disclaimer, the term of this patent is extended or adjusted under 35 U.S.C. 154(b) by 507 days.

(21) Appl. No.: 10/007,341

(22) Filed: Oct. 25, 2001

(65) Prior Publication Data

US 2002/0177957 A1 Nov. 28, 2002

Related U.S. Application Data

(60) Provisional application No. 60/243,196, filed on Oct. 25, 2000.

(51) Int. Cl.[7] ................................................ A61B 5/00
(52) U.S. Cl. ...................... 600/407; 600/410; 600/420; 600/425; 600/431; 128/920; 700/90; 702/19
(58) Field of Search ............................... 600/407, 410, 600/419, 420, 425, 431; 128/920, 922; 702/19; 700/90

(56) References Cited

U.S. PATENT DOCUMENTS

| | | | |
|---|---|---|---|
| 5,687,726 A | 11/1997 | Hoeft | |
| 5,697,371 A | 12/1997 | Aoyagi et al. | |
| 5,865,757 A | 2/1999 | Hoeft | |
| 6,275,723 B1 | 8/2001 | Ferris et al. | |
| 6,315,730 B1 | 11/2001 | Hoff et al. | |
| 6,456,862 B2 * | 9/2002 | Benni .......................... | 600/331 |

FOREIGN PATENT DOCUMENTS

WO  WO 00/57777  10/2000

OTHER PUBLICATIONS

Cenic A. et al.: "A CT Method to Measure Hemodynamics in Brain Tumors: Validation and Application of Cerebral Blood Flow Maps," American Journal of Neuroradiology, United States, Mar. 2000, pp. 462–470.

Ostergaard L. et al.: "High Resolution Measurement of Cerebral Blood Flow using Intravascular Tracer Bolus Passages. Part I: Mathematical Approach and Statistical Analysis," Magnetic Resonance in Medicine, Academic Press, Duluth, MN, US, pp. 715–725.

Database Medline Online! Jan. 1991, Cenic A. et al.: "Dynamic CT measurement of cerebral blood flow: a validation study," Database accession No. NLM9974059.

* cited by examiner

Primary Examiner—Ruth S. Smith
(74) Attorney, Agent, or Firm—Carl B. Horton, Esq.; Armstrong Teasdale LLP

(57) ABSTRACT

A method for determining tissue type includes quantitatively determining a tissue blood flow (TBF) by deconvoluting $Q(t)$ and $C_a(t)$, where $Q(t)$ represents a curve of specific mass of contrast, and $C_a(t)$ represents an arterial curve of contrast concentration, and quantitatively determining a tissue blood volume (TBV) by deconvoluting $Q(t)$ and $C_a(t)$. The method also includes quantitatively determining a tissue mean transit time (TMTT) by deconvoluting $Q(t)$ and $C_a(t)$, and quantitatively determining a tissue capillary permeability surface area product (TPS) by deconvoluting $Q(t)$ and $C_a(t)$. The method also includes determining a tissue type based on the TBF, the TBV, the TMTT, and the TPS.

14 Claims, 2 Drawing Sheets

METHOD AND APPARATUS FOR CALCULATING BLOOD FLOW PARAMETERS

CROSS REFERENCE TO RELATED APPLICATIONS

This application claims the benefit of U.S. provisional application No. 60/243,196 filed Oct. 25, 2000.

BACKGROUND OF THE INVENTION

This invention relates generally to methods and apparatus for imaging systems and, more particularly, for calculating blood flow parameters.

Stroke is a leading cause of disability among adults in North America. A National Institute for Neurological Diseases and Stroke (NINDS) trial was the first study to demonstrate that thrombolytic treatment within the first 3 hours of symptom onset is beneficial to stroke victims. However, treating patients beyond the initial 3 hours of illness with a thrombolytic treatment may carry a risk of intracranial bleeding which has resulted in a setback in the use of thrombolysis. This setback in the use of thrombolysis has prompted the realization that a more rigorous selection of patients according to certain criteria may reduce the risk of intracranial bleeding and thus, extend the therapeutic window for this therapy beyond the current 3-hour limit to benefit more patients.

BRIEF SUMMARY OF THE INVENTION

In one aspect, a method for determining tissue type is provided. The method includes quantitatively determining a tissue blood flow (TBF) by deconvoluting $Q(t)$ and $C_a(t)$, where $Q(t)$ represents a curve of specific mass of contrast, and $C_a(t)$ represents an arterial curve of contrast concentration, and quantitatively determining a tissue blood volume (TBV) by deconvoluting $Q(t)$ and $C_a(t)$. The method also includes quantitatively determining a tissue mean transit time (TMTT) by deconvoluting $Q(t)$ and $C_a(t)$, and quantitatively determining a tissue capillary permeability surface area product (TPS) by deconvoluting $Q(t)$ and $C_a(t)$. The method also includes determining a tissue type based on the TBF, the TBV, the TMTT, and the TPS.

In another aspect, a system including at least one of a computed tomography system and a nuclear magnetic resonance system is provided. The system is configured to quantitatively determine a tissue blood flow (TBF) by deconvoluting $Q(t)$ and $C_a(t)$, where $Q(t)$ represents a curve of specific mass of contrast, and $C_a(t)$ represents an arterial curve of contrast concentration, and quantitatively determine a tissue blood volume (TBV) by deconvoluting $Q(t)$ and $C_a(t)$. The system is also configured to quantitatively determine a tissue mean transit time (TMTT) by deconvoluting $Q(t)$ and $C_a(t)$, and quantitatively determine a tissue capillary permeability surface area product (TPS) by deconvoluting $Q(t)$ and $C_a(t)$. The system is also configured to determine a tissue type based on the TBF, the TBV, the TMTT, and the TPS.

In another embodiment, a computer readable medium encoded with a program executable by a computer for processing scanning data is provided. The program is configured to instruct the computer to quantitatively determine a tissue blood flow (TBF) by deconvoluting $Q(t)$ and $C_a(t)$, where $Q(t)$ represents a curve of specific mass of contrast, and $C_a(t)$ represents an arterial curve of contrast concentration, and quantitatively determine a tissue blood volume (TBV) by deconvoluting $Q(t)$ and $C_a(t)$. The program is also configured to instruct the computer to quantitatively determine a tissue mean transit time (TMTT) by deconvoluting $Q(t)$ and $C_a(t)$, and quantitatively determine a tissue capillary permeability surface area product (TPS) by deconvoluting $Q(t)$ and $C_a(t)$. The program is also configured to instruct the computer to determine a tissue type based on the TBF, the TBV, the TMTT, and the TPS.

DETAILED DESCRIPTION OF THE INVENTION

Figure 1:
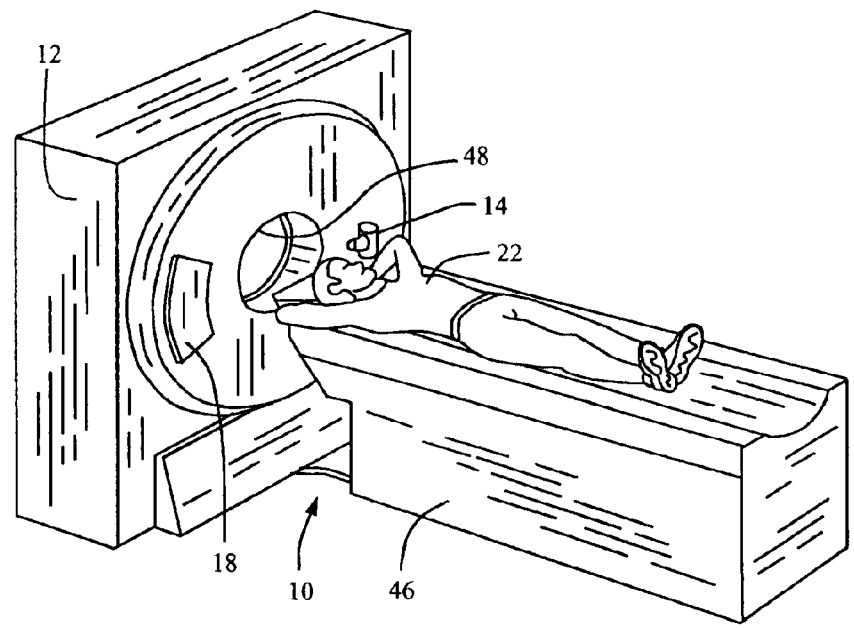
FIG. 1 is a pictorial view of a CT imaging system.

At present, there are both experimental and clinical data to suggest that the level of residual blood flow in the ischemic zone could be a useful indicator of the risk of intracranial bleeding.

The importance of absolute measurement in stroke is also predicated by the fact that there exist distinct thresholds of cerebral blood flow (CBF) for various functions of the brain. It is possible to use these thresholds to decide whether a particular brain region is salvageable, hence thrombolytics should be used to restore CBF, or is already infarcted such that thrombolysis would achieve little but instead would increase the risk of intracranial bleeding.

The brain has an intricate system of control to maintain cerebral normal limits when cerebral perfusion pressure decreases but remains within certain limits. This is achieved by dilation of the resistance blood vessels, i.e. the arterioles, vascular resistance and an increase of the cerebral blood volume (CBV). The concept of autoregulation of CBF can be used to advantage in stroke. For ischemic but viable tissue, autoregulation would lead to increased CBV so that mean transit time (MTT) is prolonged since MTT is the ratio of CBV and CBF because of the Central Volume Principle. On the other hand for ischemic but nonviable tissue, autoregulation is abolished such that both CBV and CBF are reduced but MTT may remain normal or only slightly elevated.

In summary, the absolute measurements of CBF, CBV and MTT would permit the distinction between salvageable and infarcted tissue by the following criteria:

| Ischemic Tissue Type | CBF | CBV | MTT |
| --- | --- | --- | --- |
| Viable | -- | + | ++ |
| Infarcted | -- | - | -/+ |

Wherein -- designates a large decrease, - designates a slight decrease, + designates a slight increase, ++ designates a large increase, and -/+ designates either a slight increase of a slight decrease.

It is the mismatch between CBF and CBV that discriminates salvageable and infarcted tissue. The corollary of this is that measurement of CBF alone will not reliably differentiate between viable and non-viable ischemic tissue. In addition, the ability to monitor quantitative changes in CBV may obviate the need to perform supplementary tests to evaluate the 'vascular' reserve of a stroke patient. In brief, the classical test of 'vascular' reserve evaluates the change in CBF in response to increases in pCO2 (partial pressure of CO2) in brain tissue which can be induced either by increasing inspired air concentration of CO2 or by intravenous administration of a drug, such as a carbonic anhydrase inhibitor such as, for example, Diamox. For a normal brain, raised pCO2 in tissue would induce a large increase in CBF. For ischemic tissue, where autoregulation is still intact, because CBV is already activated, the increase in CBF will be attenuated. Thus, tissue with a positive reserve is viable whereas that with little or no reserve left is at risk of infarction.

As used herein Cerebral Blood Flow (CBF) is the volume flow of blood through vasculature including the large conductance vessels, arteries, arterioles, capillaries, venules, veins and sinuses. It typically has units of ml/min/100 g. Also as used herein, Cerebral Blood Volume (CBV) is the volume of blood in the vasculature including the large conductance vessels, arteries, arterioles, capillaries, venules, veins and sinuses. It typically has units of ml/g. Additionally, as used herein Mean Transit Time (MTT) references that blood traverses the vasculature through different pathlengths such that there does not exist an unique transit time from the arterial inlet to the venous outlet. Instead there is a distribution of transit times and the mean transit time is the mean time of such a distribution. Furthermore, Minimum Transit Time (TTmin), as used herein, is the minimum time interval between entry at the arterial inlet and exit at the venous outlet of blood or contrast medium. The Central Volume Principle relates the above three quantities in the following relationship:

$$CBF = \frac{CBV}{MTT}.$$

Figure 2:
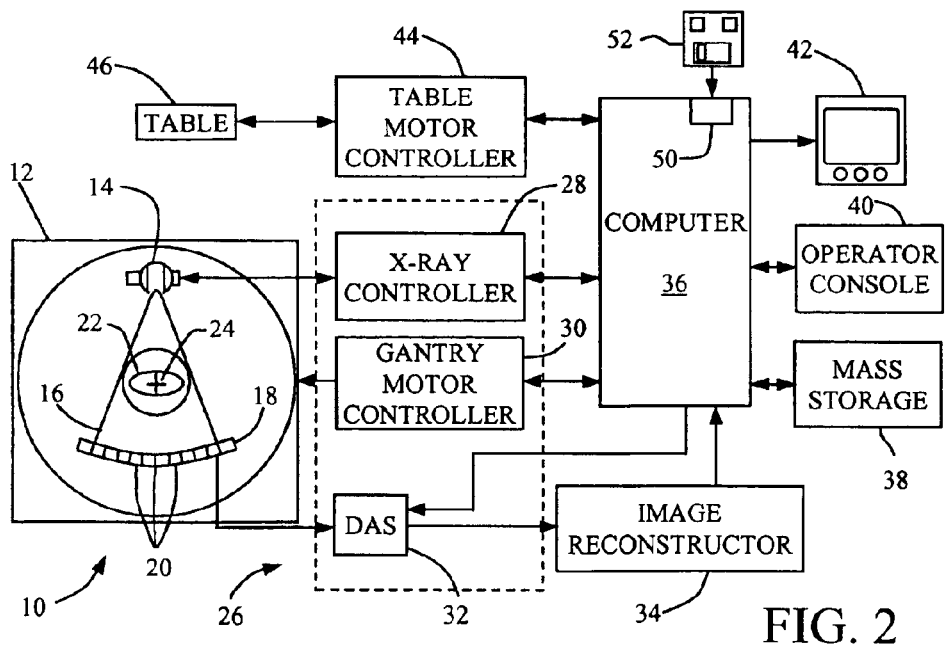
FIG. 2 is a block schematic diagram of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 so that projection data corresponding to a plurality of parallel slices are, or can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
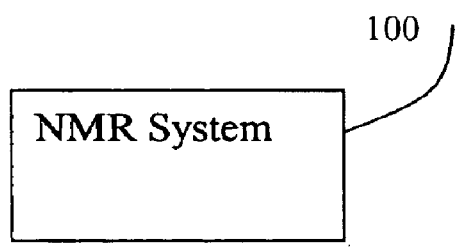
FIG. 3 is a schematic illustration of a Nuclear Magnetic Resonance (NMR) system.

In one embodiment, system 10 is used to perform CT scans and determines blood flow parameters such as Tissue Blood Flow (TBF), Tissue Blood Volume (TBV), Tissue Mean Transit Time (TMTT) and Tissue Capillary Permeability Surface Area Product (TPS) as described below. In another embodiment, a Nuclear Magnetic Resonance (NMR) system 100 (see FIG. 3) scans and determines TBF, TBV, TMTT and TPS blood flow parameters such as described below. In an exemplary embodiment, system 10 scans and determines cerebral blood flow parameters such as Cerebral Blood Flow (CBF), Cerebral Blood Volume (CBV), and Cerebral Mean Transit Time (CMTT).

In one embodiment, system 10 is used to determine tissue type. More specifically, a tissue blood flow (TBF) is quantitatively determined by deconvoluting Q(t) and Ca(t), where Q(t) represents the tissue residue function and is a curve of specific mass of contrast in tissue, and Ca(t) represents an arterial curve of contrast concentration. Also a tissue blood volume (TBV), a tissue mean transit time (TMTT), and a tissue capillary permeability surface area product (TPS) are quantitatively determined by deconvoluting Q(t) and Ca(t). In another embodiment, a Nuclear Magnetic Resonance (NMR) system 100 (see FIG. 3) scans and determines tissue type by quantitatively determining TBF, TBV, TMTT and TPS.

In one embodiment, the arterial curve of contrast concentration measured by system 10 and NMR system 100 (see FIG. 3) is corrected for partial volume averaging as described herein. For example, during a cranial scan, but not limited to cranial scans, arterial regions within the vascular territories of the cerebral arteries (anterior and middle) are identified, and used to generate the measured arterial curve of contrast concentration, $C_a'(t)$. The measured arterial curve of contrast concentration is related to the arterial curve of contrast concentration, $C_a(t)$ by $C_a'(t)=kC_a(t)$, where k is the partial volume averaging scaling factor as explained in greater detail below. A venous region either within the sagittal or tranverse sinuses is located, and $C_v(t)$ is generated where $C_v(t)=C_a(t)*h(t)$ and h(t) is the transit time spectrum of the brain, as explained herein. $C_a'(t)$ and $C_v(t)$ are deconvolved to find $$\frac{h(t)}{k}.$$

And a trailing slope of $C_a'(t)$ is extrapolated with a monoexponential function to find $C_{a,ex}'(t)$ which is convolved with $$\frac{h(t)}{k}$$

to find $C_{v,ex}(t)$. Where k is a partial volume averaging (PVA) scaling factor and is determined according to $$k = \frac{\int_0^\infty C_{a,ex}'(t)\,dt}{\int_0^\infty C_{v,ex}(t)\,dt}.$$

The measured arterial curve of contrast concentration, $C_a'(t)$, is then corrected for partial volume averaging by dividing with the factor k to arrive at the arterial curve of contrast concentration, $C_a(t)$.

A CBF and a CBV functional maps are generated with $C_a'(t)$ and divided by the PVA scaling factor, k.

In one embodiment, a convolution integral for a tissue residue function Q(t) is:

$$Q(t) = \int_0^t C_a(t-u)h(u)\,du$$

where $C_a(t)$ is an arterial curve of contrast concentration curve and h(t) is an impulse residue function. Additionally, Q(t) is equal to the convolution of $C_a(t)$ and h(t) when the system is linear and stationary. Note that when $C_a(t)=\delta(t-u)$, then the tissue residue function Q(t) is:

$$Q(t) = \int_0^t \delta(t-u)h(u)\,du = h(t)$$

This relationship lends itself to the following interpretation of the convolution integral, e.g.

$$C_a(t) = \sum_n C_a(t - n\Delta t)\delta(t - n\Delta t),$$

therefore the tissue residue function Q(t) is:

$$Q(t) = \int_0^t C_a(t-u)h(u)\,du, \quad \text{which is}$$

$$= \int_0^t \sum_n [C_a(t-u)\delta(t-u-n\Delta t)]h(u)\,du, \quad \text{which is}$$

$$= \sum_n \int_0^t C_a(t-u)\delta(t-u-n\Delta t)h(u)\,du, \quad \text{which is}$$

$$= \sum_n C_a(n\Delta t)h(t - n\Delta t).$$

A discretization of the tissue residue function convolution integral is determined by dividing a time interval [0,t] into m equal intervals of length $\Delta t$, each using the rectangular rule for quadrature of the convolution integral, according to:

$$Q(t) = Q(m\Delta t) = \sum_{i=0}^{m-1} C_a([m-i]\Delta t)h(i\Delta t)\Delta t.$$

In a matrix notation, the convolution integral for the tissue residue function after discretization is Q=Ah and therefore Q=Ah is:

$$\begin{pmatrix} Q(\Delta t) \\ Q(2\Delta t) \\ \vdots \\ Q((M-1)\Delta t) \\ Q(M\Delta t) \end{pmatrix} = \begin{bmatrix} C_a(\Delta t) & 0 & 0 & \cdots & \cdots & 0 \\ C_a(2\Delta t) & C_a(\Delta t) & 0 & 0 & \cdots & 0 \\ \vdots & \vdots & \vdots & \vdots & \vdots & \vdots \\ C_a((M-1)\Delta t) & C_a((M-2)\Delta t) & \cdots & \cdots & \cdots & C_a(M-N)\Delta t) \\ C_a(M\Delta t) & C_a((M-1)\Delta t) & C_a((M-2)\Delta t) & \cdots & \cdots & C_a((M-N+1))\Delta t \end{bmatrix} \begin{pmatrix} h(0) \\ h(\Delta t) \\ h(2\Delta t) \\ \vdots \\ h((N-1)\Delta t) \end{pmatrix}$$

where Q is a M×1 vector, A is a M×N matrix, and h is a N×1 vector. A least squares solution, $\hat{h}$, of Q=Ah facilitates minimizing the norm of a tissue residue vector, $r=Q-A\hat{h}$ according to: $\|r\|^2 = \|Q-A\hat{h}\|^2$.

In one embodiment, an equality constraint is incorporated into the least squares problem such that when h is the impulse residue function of a linear and stationary flow system, it will satisfy the time causality, i.e. if the injection of tracer does not occur at time zero, then some beginning elements of h should be set to zero (time causality), and defining a minimum transit time, i.e. h will have a plateau of a duration equal to the minimum transit time. The requirement for time causality and minimum transit time can be written as the following equalities:

$$h_1 = 0$$

$$h_2 = 0$$

$$\vdots$$

$$h_I = 0$$

$$h_{I+1} = h_{I+2}$$

$$h_{I+2} = h_{I+3}$$

$$\vdots$$

$$h_{I+L-1} = h_{I+L}$$

where the first I elements of h are zero, and the duration of the plateau is (L−1) dt, where dt is the sampling interval of each element of h. The equality constraints can be written compactly as the matrix equation Ch=b:

$$C = \begin{array}{c} I \\ L-1 \end{array} \left[ \begin{array}{ccccc|cccccc|cccccccccc} \multicolumn{5}{c|}{I} & \multicolumn{6}{c|}{L} & \multicolumn{10}{c}{N-I-L} \\ 1 & 0 & \cdots & 0 & & 0 & 0 & 0 & \cdots & 0 & 0 & 0 & \cdots & \cdots & \cdots & \cdots & \cdots & \cdots & \cdots & 0 \\ 0 & 1 & \cdots & 0 & & 0 & 0 & 0 & \cdots & 0 & 0 & 0 & \cdots & \cdots & \cdots & \cdots & \cdots & \cdots & \cdots & 0 \\ \vdots & \vdots & \cdots & \vdots & & \vdots & \vdots & \vdots & \cdots & \vdots & \vdots & \vdots & \cdots & \cdots & \cdots & \cdots & \cdots & \cdots & \cdots & \vdots \\ 0 & 0 & \cdots & 1 & & 0 & 0 & 0 & \cdots & 0 & 0 & 0 & \cdots & \cdots & \cdots & \cdots & \cdots & \cdots & \cdots & 0 \\ \hline 0 & 0 & \vdots & 0 & & 1 & -1 & 0 & \cdots & 0 & 0 & 0 & \cdots & \cdots & \cdots & \cdots & \cdots & \cdots & \cdots & 0 \\ 0 & 0 & \vdots & 0 & & 0 & 1 & -1 & \cdots & 0 & 0 & 0 & \cdots & \cdots & \cdots & \cdots & \cdots & \cdots & \cdots & 0 \\ \vdots & \vdots & \vdots & \vdots & & \vdots & \vdots & \vdots & \cdots & \vdots & \vdots & \vdots & \cdots & \cdots & \cdots & \cdots & \cdots & \cdots & \cdots & \vdots \\ 0 & 0 & \cdots & 0 & & 0 & 0 & 0 & \cdots & 1 & -1 & 0 & \cdots & \cdots & \cdots & \cdots & \cdots & \cdots & \cdots & 0 \end{array} \right]$$

where C is a $M_1 \times N$ matrix, h is the impulse residue function, and b=0 is a $N \times 1$ zero vector. Note that $M_1$-I+L-1. Also C can be partitioned as:

$$\begin{array}{c} I \\ L-1 \end{array} \left[ \begin{array}{cccccccc|cccccccc} \multicolumn{8}{c|}{c_1} & \multicolumn{8}{c}{c_2} \\ 1 & 0 & \cdots & 0 & 0 & 0 & 0 & \cdots & 0 & 0 & 0 & \cdots & \cdots & \cdots & \cdots & \cdots & \cdots & \cdots & 0 \\ 0 & 1 & \cdots & 0 & 0 & 0 & 0 & \cdots & 0 & 0 & 0 & \cdots & \cdots & \cdots & \cdots & \cdots & \cdots & \cdots & 0 \\ \vdots & \vdots & \cdots & \vdots & \vdots & \vdots & \vdots & \cdots & 0 & \vdots & \vdots & \cdots & \cdots & \cdots & \cdots & \cdots & \cdots & \cdots & \vdots \\ 0 & 0 & \cdots & 1 & 0 & 0 & 0 & \cdots & 0 & 0 & 0 & \cdots & \cdots & \cdots & \cdots & \cdots & \cdots & \cdots & 0 \\ \hline 0 & 0 & \vdots & 0 & 1 & -1 & 0 & \cdots & 0 & 0 & 0 & \cdots & \cdots & \cdots & \cdots & \cdots & \cdots & \cdots & 0 \\ 0 & 0 & \vdots & 0 & 0 & 1 & -1 & \cdots & 0 & 0 & 0 & \cdots & \cdots & \cdots & \cdots & \cdots & \cdots & \cdots & 0 \\ \vdots & \vdots & \vdots & \vdots & \vdots & \vdots & \vdots & \cdots & \vdots & \vdots & \vdots & \cdots & \cdots & \cdots & \cdots & \cdots & \cdots & \cdots & \vdots \\ 0 & 0 & \cdots & 0 & 0 & 0 & 0 & \cdots & 1 & -1 & 0 & \cdots & \cdots & \cdots & \cdots & \cdots & \cdots & \cdots & 0 \end{array} \right]$$

where $C_1$ is a $M_1 \times M_1$ square matrix with full rank, and $C_2$ is a $M_1 \times (N-M_1)$ matrix with only one nonzero element, wherein the nonzero element $(M_1+1, 1)$th element is equal to $-1$. Similarly h can be partitioned as:

$$h = \begin{pmatrix} h_1 \\ h_2 \end{pmatrix},$$

where $h_1$ is a $M_1 \times 1$ vector of the first $M_1$ elements of h and $h_2$ is a $N-M_1 \times 1$ vector of the remaining elements.

With these partitions of C and h, the constraint equation, Ch=b, can be written as:

$$[C_1 \ C_2] \begin{pmatrix} h_1 \\ h_2 \end{pmatrix} = b \Rightarrow C_1 h_1 = (b - C_2 h_2).$$

Since $C_1$ is square and of full rank, its inverse exists, then the constraint equation can be written as: $h_1 = C_1^{-1}(b - C_2 h_2)$, where the inverse of $C_1$ is:

$$C_1^{-1} = \begin{array}{c} I \\ L-1 \end{array} \left[ \begin{array}{cccc|cccccc} \multicolumn{4}{c|}{I} & \multicolumn{6}{c}{L-1} \\ 1 & 0 & \cdots & 0 & 0 & 0 & 0 & 0 & 0 \\ 0 & 1 & \cdots & 0 & 0 & 0 & 0 & 0 & 0 \\ \vdots & \vdots & \ddots & \vdots & \vdots & \vdots & \vdots & \vdots & \vdots \\ 0 & 0 & \cdots & 1 & 0 & 0 & 0 & 0 & 0 \\ \hline 0 & 0 & 0 & 0 & 1 & 1 & \cdots & 1 & 1 \\ 0 & 0 & 0 & 0 & 0 & 1 & \cdots & 1 & 1 \\ \vdots & \vdots & \vdots & \vdots & \vdots & \vdots & \ddots & \vdots & \vdots \\ 0 & 0 & 0 & 0 & 0 & 0 & 0 & 1 & 1 \\ 0 & 0 & 0 & 0 & 0 & 0 & 0 & 0 & 1 \end{array} \right]$$

As a check, $h_1 = C_1^{-1}(b - C_2 h_2)$ is evaluated to ensure that it does not violate the constraint described herein. For example, since b is a zero vector, $h_1$ can be simplified as: $h_1 = -C_1^{-1} C_2 h_2$. As stated previously herein, $C_2$ is a $M_1 \times N-M_1$ matrix of the form:

$$C_2 = \begin{bmatrix} 0 & 0 & \cdots & 0 \\ 0 & 0 & \cdots & 0 \\ \vdots & \vdots & \vdots & \vdots \\ 0 & 0 & \cdots & 0 \\ 0 & 0 & \cdots & 0 \\ 0 & 0 & \cdots & 0 \\ \vdots & \vdots & \vdots & \vdots \\ 0 & 0 & \cdots & 0 \\ -1 & 0 & \cdots & 0 \end{bmatrix} = \begin{bmatrix} \overset{1}{\phantom{0}} & \overset{N-M_1-1}{\phantom{0}} \\ 0 & 0 & 0 & \cdots & 0 \\ 0 & 0 & 0 & \cdots & 0 \\ \vdots & \vdots & \vdots & \vdots \\ 0 & 0 & 0 & \cdots & 0 \\ -1 & 0 & 0 & \cdots & 0 \end{bmatrix} = \begin{bmatrix} 0 & 0 \\ -1 & 0 \end{bmatrix}$$

and $h_2$ can be partitioned as:

$$h_2 = \begin{pmatrix} h_{M_1+1} \\ h_{M_1+2} \\ \vdots \\ h_N \end{pmatrix} = \begin{pmatrix} h_{M_1+1} \\ h_2 \end{pmatrix}$$

then, $$C_2 h_2 = \begin{bmatrix} \overset{1}{\phantom{0}} & \overset{N-M_i-1}{\phantom{0}} \\ 0 & 0 \\ -1 & 0 \end{bmatrix} \begin{matrix} M_i-1 \\ 1 \end{matrix} \begin{pmatrix} h_{M_i+1} \\ h_2 \end{pmatrix} \begin{matrix} 1 \\ N-M_i-1 \end{matrix}$$

$$= \begin{pmatrix} 0 \\ -h_{M_i+1} \end{pmatrix} \begin{matrix} M_i-1 \\ 1 \end{matrix} \text{ and,}$$

-continued $$h_1 = \begin{pmatrix} h_1 \\ h_2 \\ \vdots \\ h_I \\ h_{I+1} \\ h_{I+2} \\ \vdots \\ h_{I+L} \end{pmatrix} = -C_1^{-1}\begin{pmatrix} O \\ -h_{M_i+1} \end{pmatrix}$$

$$= \begin{bmatrix} 1 & \begin{bmatrix} \frac{1}{0} \\ 0 \\ \vdots \\ \frac{X}{X} & 0 \\ -1 \\ -1 \\ \vdots \\ -1 \end{bmatrix} \\ L-1 \end{bmatrix} \begin{pmatrix} O \\ -h_{M_i+1} \end{pmatrix} \begin{matrix} M_i-1 \\ 1 \end{matrix}$$

$$= \begin{pmatrix} 0 \\ 0 \\ \vdots \\ 0 \\ h_{M_i+1} \\ h_{M_i+1} \\ \vdots \\ h_{M_i+1} \end{pmatrix} \begin{matrix} I \\ L-1 \end{matrix}$$

as the time causality and minimum transit time constraints required.

In one embodiment, the equality constraint Ch=b affect on the solution of the least squares problem Q=Ah can be determined according to: First, A is partitioned in the same way as C:

$$A = M\begin{bmatrix} M_1 & N-M_1 \\ A_1, & A_2 \end{bmatrix},$$

then Ah can be written as:

$$Ah = [A_1, A_2]\begin{pmatrix} h_1 \\ h_2 \end{pmatrix} =$$

$$A_1h_1 + A_2h_2 = A_1(-C_1^{-1}C_2h_2) + A_2h_2 = (A_2 - A_1C_1^{-1}C_2)h_2.$$

Therefore with the equality constraint, Ch=b, the least squares problem Ah=Q is equivalent to the 'reduced' problem of $(A_2-A_1C_1^{-1}C_2)h_2=Q$ or in short $A_rh_2=Q$ where $A_r=(A_2-A_1C_1^{-1}C_2)$.

From the least squares solution, $\hat{h}_2$, of the reduced problem $A_rh_2=Q$, the full impulse residue function, h, can be reconstituted by:

$$h = \begin{pmatrix} h_1 \\ \hat{h}_2 \end{pmatrix}$$

and $h_1$ is a (I+L−1)×1 vector whose first I elements are zero and the subsequent L−1 elements are equal to the first element of $\hat{h}_2$.

For example, for the evaluation of $A_2-A_1C_1^{-1}C_2$ $$C_1^{-1}C_2 = M_1-1 \begin{bmatrix} \frac{M_1-1}{X} & \frac{1}{0} \\ 0 & \\ \vdots & M_1-1 \\ X & 0 \\ 1 & \\ \vdots & \\ 1 & \end{bmatrix} \begin{bmatrix} \frac{1}{0} & \frac{N-M_1-1}{0} \\ 0 & \\ \vdots & 0 \\ 0 & \\ -1 & 0 \cdots 0 \end{bmatrix}$$

$$= M_1-1 \begin{bmatrix} \frac{1}{0} & \frac{N-M_1-1}{0 \cdots 0} \\ 0 & \\ \vdots & 0 \\ 0 & \\ -1 & \\ \vdots & \\ -1 & \end{bmatrix} = \begin{matrix} M_1-L+1 \\ L-1 \end{matrix} \begin{bmatrix} 1 & \frac{N-M_1-1}{0} \\ 0 & 0 \\ \vdots & \\ 0 & \\ -1 & \\ \vdots & 0 \\ -1 & \end{bmatrix}$$

where X is a plurality of partitions of matrices that are not used. $A_1$ is then partitioned according to:

$$A_1 = \begin{matrix} M-L+1 \\ L-1 \end{matrix} \begin{bmatrix} \frac{M_1-L+1}{X} & \frac{L-1}{T_1} \\ X & T_2 \end{bmatrix}$$

such that:

$$A_1C_1^{-1}C_2 =$$

$$\begin{matrix} M-L+1 \\ L-1 \end{matrix} \begin{bmatrix} \frac{M_1-L+1}{X} & \frac{L-1}{T_1} \\ X & T_2 \end{bmatrix}^{M_1-L+1} \begin{bmatrix} \frac{1}{0} & \frac{N-M_1-1}{0} \\ 0 & \\ \vdots & 0 \\ 0 & \\ -1 & \\ \vdots & 0 \\ -1 & \end{bmatrix} = \begin{matrix} M-L+1 \\ L-1 \end{matrix} \begin{bmatrix} T_1\begin{pmatrix}-1\\\vdots\\-1\end{pmatrix} & \frac{N-M_1-1}{0} \\ T_2\begin{pmatrix}-1\\\vdots\\-1\end{pmatrix} & 0 \end{bmatrix}$$

therefore, $A_2-A_1C_1^{-1}C_2$ is the same as $A_2$ except that its first column is modified by adding the M×1 vector $$\begin{matrix} M-L+1 \\ L-1 \end{matrix} \begin{bmatrix} T_1\begin{pmatrix}1\\\vdots\\1\end{pmatrix} \\ T_2\begin{pmatrix}1\\\vdots\\1\end{pmatrix} \end{bmatrix}$$

to it.

In one embodiment, a smoothness constraint by Lagrange Multiplier is incorporated into the least squares solution of the reduced problem $A_rh_2=Q$. In fact, if h is the impulse residue function of a physiologically realizable flow system, then its elements would change smoothly. In one embodiment, a matrix γF is appended to $A_r=(A_2-A_1C_1^{-1}C_2)$ and vector γd to Q to the reduced problem to obtain:

$$\begin{pmatrix} q \\ \gamma d \end{pmatrix} = \begin{bmatrix} A_r \\ \gamma S \end{bmatrix} h_2 \Leftrightarrow p = Eh_2 \text{ where } p = \begin{pmatrix} q \\ \gamma d \end{pmatrix}$$

is a $M_2 \times 1$ vector and $$E = \begin{bmatrix} A_r \\ \gamma S \end{bmatrix}$$

is a $M_2 \times (N-M_1)$ matrix, and $p=Eh_2$ is referred to the appended reduced problem.

The least squares solution, $\hat{h}_2$, of the appended reduced problem $p=Eh_2$ facilitates minimizing the normal of the residual vector according to:

$$\|r\|^2 = \left(\begin{pmatrix} Q \\ \gamma d \end{pmatrix} - \begin{bmatrix} A_r \\ \gamma S \end{bmatrix} \hat{h}_2\right)^T \left(\begin{pmatrix} Q \\ \gamma d \end{pmatrix} - \begin{bmatrix} A_r \\ \gamma S \end{bmatrix} \hat{h}_2\right)$$

$$= \left([Q^T \ \gamma d^T] - \hat{h}_2^T [A_r^T \ \gamma S^T]\right)\left(\begin{pmatrix} Q \\ \gamma d \end{pmatrix} - \begin{bmatrix} A_r \\ \gamma S \end{bmatrix} \hat{h}_2\right)$$

$$= [Q^T \ \gamma d^T]\begin{pmatrix} Q \\ \gamma d \end{pmatrix} - \hat{h}_2^T [A_r^T \ \gamma S^T]\begin{pmatrix} Q \\ \gamma d \end{pmatrix} - [Q^T \ \gamma d^T]\begin{bmatrix} A_r \\ \gamma S \end{bmatrix}\hat{h}_2 +$$

$$\hat{h}_2^T [A_r^T \ \gamma S^T]\begin{bmatrix} A_r \\ \gamma S \end{bmatrix}\hat{h}_2$$

$$= Q^T Q + \gamma^2 d^T d - \hat{h}_2^T A_r^T Q - \gamma^2 \hat{h}_2^T S^T d - Q^T A_r \hat{h}_2 - \gamma^2 d^T S \hat{h}_2 +$$

$$\hat{h}_2^T A_r^T A_r \hat{h}_2 + \gamma^2 \hat{h}_2^T S^T F \hat{h}_2$$

$$= Q^T Q - \hat{h}_2^T A_r^T Q - q^T A_r \hat{h}_2 + \hat{h}_2^T A_r^T A_r \hat{h}_2 +$$

$$\gamma^2 \left[d^T d - \hat{h}_2^T F^T d - d^T F \hat{h}_2 + \hat{h}_2^T F^T F \hat{h}_2\right]$$

$$= \|Q - A_r \hat{h}_2\|^2 + \gamma^2 \|d - S\hat{h}_2\|^2$$

where $\gamma$ is the Lagrange multiplier and determines the relative weighting the least squares solution of the reduced problem places in minimizing $\|Q-A_r\hat{h}_2\|^2$ and $\|d-F\hat{h}_2\|^2$. If $\gamma$ is large, then the solution will minimize $\|d-F\hat{h}_2\|^2$ more than $\|Q-A_r\hat{h}_2\|^2$.

The smoothness of the least squares estimate $\hat{h}_2$ of the appended reduced problem can be gauged by the norm of its second derivative with respect to time according to:

$$\hat{h}_2 = \begin{pmatrix} \hat{h}_2(1) \\ \hat{h}_2(2) \\ \vdots \\ \hat{h}_2(N-M_1) \end{pmatrix} \quad \frac{d\hat{h}_2}{dt} = \frac{1}{\Delta t}\begin{pmatrix} \hat{h}_2(1) - \hat{h}_2(0) \\ \hat{h}_2(2) - \hat{h}_2(1) \\ \vdots \\ \hat{h}_2(N-M_1) - \hat{h}_2(N-M_1-1) \end{pmatrix} =$$

$$\frac{1}{\Delta t}\begin{pmatrix} \hat{h}_2(1) \\ \hat{h}(2) - \hat{h}(1) \\ \vdots \\ \hat{h}_2(N-M_1) - \hat{h}_2(N-M_1-1) \end{pmatrix}$$

$$\frac{d^2 \hat{h}_2}{dt^2} = \frac{1}{\Delta t^2}\begin{pmatrix} \hat{h}_2(1) - 2\hat{h}_2(0) + \hat{h}_2(-1) \\ \hat{h}_2(2) - 2\hat{h}_2(1) + \hat{h}_2(-1) \\ \vdots \\ \hat{h}_2(N-M_1) - 2\hat{h}_2(N-M_1-1) + \hat{h}_2(N-M_1-2) \end{pmatrix} =$$

$$\frac{1}{\Delta t^2}\begin{pmatrix} \hat{h}_2(1) \\ \hat{h}_2(2) - 2\hat{h}_2(1) \\ \vdots \\ \hat{h}_2(N-M_1) - 2\hat{h}_2(N-M_1-1) + \hat{h}_2(N-M_1-2) \end{pmatrix} =$$

$$\frac{1}{\Delta t^2}\begin{bmatrix} 1 & 0 & 0 & 0 & \cdots & 0 & 0 & 0 & 0 & 0 \\ -2 & 1 & 0 & 0 & \cdots & 0 & 0 & 0 & 0 & 0 \\ 1 & -2 & 1 & 0 & \cdots & 0 & 0 & 0 & 0 & 0 \\ 0 & 1 & -2 & 1 & \cdots & 0 & 0 & 0 & 0 & 0 \\ & & & & \cdots & & & & & \\ 0 & 0 & 0 & 0 & \cdots & 0 & 1 & -2 & 1 & 0 \\ 0 & 0 & 0 & 0 & \cdots & 0 & 0 & 1 & -2 & 1 \end{bmatrix}\begin{pmatrix} \hat{h}_2(1) \\ \hat{h}_2(2) \\ \hat{h}_2(3) \\ \vdots \\ \hat{h}_2(N-M_1-2) \\ \hat{h}_2(N-M_1-1) \\ \hat{h}(N-M_1) \end{pmatrix}$$

To incorporate the smoothness constraint, the matrix S is set according to:

$$S = \frac{1}{\Delta t^2}\begin{bmatrix} 1 & 0 & 0 & 0 & \cdots & 0 & 0 & 0 & 0 & 0 \\ -2 & 1 & 0 & 0 & \cdots & 0 & 0 & 0 & 0 & 0 \\ 1 & -2 & 1 & 0 & \cdots & 0 & 0 & 0 & 0 & 0 \\ 0 & 1 & -2 & 1 & \cdots & 0 & 0 & 0 & 0 & 0 \\ & & & & \cdots & & & & & \\ 0 & 0 & 0 & 0 & \cdots & 0 & 1 & -2 & 1 & 0 \\ 0 & 0 & 0 & 0 & \cdots & 0 & 0 & 1 & -2 & 1 \end{bmatrix}$$

where $d=0$. The least square solution of the appended reduced problem facilitates minimizing both $\|Q-A_r\hat{h}_2\|^2$ and $\|S\hat{h}_2\|^2$ with the relative weighting controlled by $\gamma$.

In one embodiment, an inequality constraint is imposed on the solution of the appended reduced problem. The appended reduced problem is:

$$\begin{pmatrix} Q \\ \gamma d \end{pmatrix} = \begin{bmatrix} A_r \\ \gamma S \end{bmatrix} h_2$$

which can be written as: $p=Eh_2$.

In another embodiment, the least squares estimate of the appended problem under the linear inequality constraint $Gh_2 \geq b$ is determined. The dimension of the appended matrix E is $M_2 \times (N-M_1)$. In one embodiment, E has a rank of $K \leq (N-M_1)$ and has the following singular value decomposition:

$$E = U\begin{bmatrix} S & 0 \\ 0 & 0 \end{bmatrix} V^T$$

where S is a $K \times K$ diagonal matrix with its diagonal entries equal to the singular values of E, U and V are orthogonal matrices of dimensions $M_2 \times M_2$ and $(N-M_1) \times (N-M_1)$ respectively. The least squares solution, $\hat{h}_2$, of the appended reduced problem $p=Eh_2$ will minimize $\|Eh_2-p\|^2$.

Using the singular value decomposition of E, $\|Eh_2-p\|^2$ can be simplified as:

$$\|Eh_2 - p\|^2 = \left\| U \begin{bmatrix} S & 0 \\ 0 & 0 \end{bmatrix} V^T h_2 - p \right\|^2 = \left\| U^T U \begin{bmatrix} S & 0 \\ 0 & 0 \end{bmatrix} V^T h_2 - U^T p \right\|^2, \text{ Since } U^T \text{ is orthogonal}$$

$$= \left\| \begin{bmatrix} S & 0 \\ 0 & 0 \end{bmatrix} V^T h - U^T p \right\|^2 = \left\| \begin{bmatrix} S & 0 \\ 0 & 0 \end{bmatrix} \begin{bmatrix} V_1^T \\ V_2^T \end{bmatrix} h_2 - \begin{bmatrix} U_1^T \\ U_2^T \end{bmatrix} p \right\|^2 = \left\| \begin{bmatrix} SV_1^T h_2 \\ 0 \end{bmatrix} - \begin{bmatrix} U_1^T p \\ U_2^T p \end{bmatrix} \right\|^2$$

$$= \left\| \begin{bmatrix} SV_1^T h_2 - U_1^T p \\ -U_2^T p \end{bmatrix} \right\|^2 = \|SV_1^T h_2 - U_1^T p\|^2 + \|U_2^T p\|^2$$

Since $\|U_2^T p\|^2$ is constant, minimizing $\|Eh_2-p\|^2$ is equivalent to minimizing $\|SV_1^T h_2 - U_1^T p\|^2$.

In one embodiment, the variable $h_2$ is changed to z such that $z = SV_1^T h_2 - U_1^T p \Leftrightarrow V_1^T h_2 = S^{-1} z + S^{-1} U_1^T p$.

Minimizing $\|Eh_2-p\|^2$ is the same as minimizing $\|z\|^2$ and, therefore the inequality constraint becomes:

$Gh_2 \geq b$ $\Leftrightarrow G(V_1 V_1^T + V_2 V_2^T) h_2 \geq b$ $\Leftrightarrow GV_1(S^{-1}z + S^{-1}U_1^T p) + GV_2 V_2^T h_2 \geq b$ $\Leftrightarrow GV_1(S^{-1}z + S^{-1}U_1^T p) + GV_2 V_2^T V_1(S^{-1}z + S^{-1}U_1^T p) \geq b$ $\Leftrightarrow GV_1 S^{-1} z + GV_2 V_2^T S^{-1} z \geq b - GV_1 S^{-1} U_1^T p - GV_2 V_2^T V_1 S^{-1} U_1^T p$ $\Leftrightarrow G(I_2 + V_2 V_2^T) V_1 S^{-1} z \geq b - G(I_2 + V_2 V_2^T) V_1 S^{-1} U_1^T p$ Therefore, the problem of minimizing $\|Eh_2-p\|^2$ subject to the constraint $Gh_2 \geq b$ is equivalent to minimizing $\|z\|^2$ subject to $G(I_2 + V_2 V_2^T) V_1 S^{-1} z \geq b - G(I_2 + V_2 V_2^T) V_1 S^{-1} U_1^T p$. From the solution $\hat{z}$, that minimize $\|z\|^2$, the corresponding least squares solution, $\hat{h}_2$, of the appended reduced problem $Eh_2 = p$ can be found by the inversion of the equation $z = SV_1^T h_2 - U_1^T p$. From the least squares solution, $\hat{h}_2$, of the appended reduced problem, $Eh_2 = p$, the full impulse residue function, h, can be reconstituted by:

$$h = \begin{pmatrix} h_1 \\ \hat{h}_2 \end{pmatrix}$$

and $h_1$ is a $(I+L-1) \times 1$ vector whose first I elements are zero and the subsequent L-1 elements are equal to the first element of $\hat{h}_2$.

In another embodiment, E has a rank of $K = (N - M_1)$ and has the following singular value decomposition:

$$E = U \begin{bmatrix} S \\ 0 \end{bmatrix} V^T,$$

where S is a K×K diagonal matrix with its diagonal entries equal to the singular values of E, U and V are orthogonal matrices of dimensions $M_2 \times M_2$ and $(N-M_1) \times (N-M_1)$ respectively. The least squares solution, $\hat{h}_2$, of the appended reduced problem $f = Eh_2$ facilitates minimizing $\|Eh_2 - p\|^2$.

Using a singular value decomposition of E, $\|Eh_2-p\|^2$ can be simplified as:

$$\|Eh_2 - p\|^2 = \left\| U \begin{bmatrix} S \\ 0 \end{bmatrix} V^T h_2 - p \right\|^2 = \left\| U^T U \begin{bmatrix} S \\ 0 \end{bmatrix} V^T h_2 - U^T p \right\|^2, \text{ Since } U^T \text{ is orthogonal}$$

$$= \left\| \begin{bmatrix} S \\ 0 \end{bmatrix} V^T h_2 - U^T p \right\|^2 = \left\| \begin{bmatrix} S \\ 0 \end{bmatrix} V^T h_2 - \begin{bmatrix} U_1^T \\ U_2^T \end{bmatrix} p \right\|^2 = \left\| \begin{bmatrix} SV^T h_2 \\ 0 \end{bmatrix} - \begin{bmatrix} U_1^T p \\ U_2^T p \end{bmatrix} \right\|^2$$

$$= \left\| \begin{bmatrix} SV^T h_2 - U_1^T p \\ -U_2^T p \end{bmatrix} \right\|^2 = \|SV^T h_2 - U_1^T p\|^2 + \|U_2^T p\|^2$$

since $\|U_2^T p\|^2$ is constant, minimizing $\|Eh_2-p\|^2$ is equivalent to minimizing $\|SV^T h_2 - U_1^T p\|^2$. In one embodiment, the variable $h_2$ is changed to z such that: $z = SV^T h_2 - U_1^T p \Leftrightarrow V^T h_2 = S^{-1} z + S^{-1} U_1^T p$ Minimizing $\|Eh_2-p\|^2$ is the same as minimizing $\|z\|^2$ and the inequality constraint becomes:

$$Gd_2 \geq b$$
$$\Leftrightarrow G(VV^T)h_2 \geq b$$
$$\Leftrightarrow GV(S^{-1}z+S^{-1}U_1^T p) \geq b$$
$$\Leftrightarrow GVS^{-1}z \geq b - GVS^{-1}U_1^T p$$

Minimizing $\|Eh_2-p\|^2$ subject to the constraint $Gh_2 \geq b$ is equivalent to minimizing $\|z\|^2$ subject to $GVS^{-1}z \geq b - GVS^{-1}U_1^T p$.

A formulation of smoothness, nonnegative and monotonicity constraints for the reduced problem can now be stated. The least squares solution of the reduced problem: $Q = A_r h_2$ with the smoothness, nonnegative and monotonicity constraints can be recast as the least squares solution of the appended reduced problem according to:

$$\begin{pmatrix} q \\ \gamma d \end{pmatrix} = \begin{bmatrix} A_r \\ \gamma S \end{bmatrix} h_2 \text{ or } p = Eh_2$$

with the constraint $I_{(N-M_1) \times (N-M_1)} h_2 \geq 0$ and, $Dh_2 \geq 0$, where D is a $(N-M_1-1) \times (N-M_1)$ matrix of the form:

$$D = \begin{bmatrix} 1 & -1 & 0 & \cdots & \cdots & \cdots & 0 & 0 & 0 \\ 0 & 1 & -1 & \cdots & \cdots & \cdots & 0 & 0 & 0 \\ \vdots & \vdots & \vdots & \vdots & \vdots & \vdots & \vdots & \vdots & \vdots \\ \vdots & \vdots & \vdots & \vdots & \vdots & \vdots & \vdots & \vdots & \vdots \\ 0 & 0 & 0 & \cdots & \cdots & \cdots & 1 & -1 & 0 \\ 0 & 0 & 0 & \cdots & \cdots & \cdots & 0 & 1 & -1 \end{bmatrix}$$

such that $Dh_2 \geq 0$ is equivalent to $h_2(1) \geq h_2(2) \geq \ldots h_2(N-M_1)$.

The two inequality constraints $I_{(N-M_1) \times (N-M_1)} h_2 \geq 0$ and $Dh_2 \geq 0$ can be combined into $$\begin{bmatrix} I_{(N-M_1) \times (N-M_1)} \\ D_{(N-M_1-1) \times (N-M_1)} \end{bmatrix} h_2 \geq 0$$

or, $Gh_2 \geq 0$ where G is a $2(N-M_1-1) \times (N-M_1)$ matrix as defined herein such that $I_{(N-M_1) \times (N-M_1)}$ is an $(N-M_1) \times (N-M_1)$ identity matrix.

The least squares solution of the appended reduced problem $p = Eh_2$ subject to the nonnegative and montonicity constraints can be determined using the method described herein. From the least squares solution, $\hat{h}_2$, of the appended reduced problem, $Eh_2 = p$, the full impulse residue function, h, can be reconstituted by:

$$h = \begin{pmatrix} h_1 \\ \hat{h}_2 \end{pmatrix}$$

and $h_1$ is a $(I+L-1) \times 1$ vector whose first I elements are zero and the subsequent L-1 elements are equal to the first element of $\hat{h}_2$.

In one embodiment, in tissue where there is no leakage of contrast from the blood stream into the interstitial space, for example, the brain with intact blood-brain-barrier, the reconstituted full impulse residue function h(t) can be used to determine Tissue Blood Flow (TBF) as the peak height of h(t), Tissue Blood Volume (TBV) as the area underneath h(t) and Tissue Mean Transit Time (TMTT) as the TBV divided by TBF.

In one embodiment, in tissue where there is leakage of contrast from the blood stream into the interstitial space, the impulse residue function h(t) can be modeled by the Johnson-Wilson model.

An adiabatic approximation of the Johnson-Wilson Model is then used to parameterize the impulse residue function in terms of TBF, TBV, TMTT and TPS. In one embodiment, the impulse residue function for the adiabatic approximation of the Johnson-Wilson model is:

$$R(t) = \begin{cases} 0.0 & t \leq t_o \\ 1.0 & t_o \leq t \leq t_o + W \\ Ee^{-k(t-t_o-W)} & t \geq t_o + W \end{cases} \quad (1)$$

where $t_o$ is a time delay between an arterial curve of contrast concentration, $C_a(t)$, and the tissue residue function, Q(t), W is the tissue mean transit time (TMTT), and k is the rate constant of the exponential function and is defined according to:

$$k = \frac{FE}{V_e} \quad (2)$$

where F is the Tissue Blood Flow (TBF), E is the extraction efficiency of contrast material from blood and $V_e$ is the distribution space of contrast material in the intersitial space. Tissue Blood Volume is equal to TBF×TMTT. Tissue capillary permeability surface area product (TPS) is: $-\ln(1-E)$.

The tissue residue function, Q(t), is given by:

$$Q(t) = F \cdot [C_a(t) * R(t)] \quad (3)$$

where * is the convolution operation.

The linearization of the tissue residue function (or the expression of the tissue residue function or some t function of it in terms of linear functions of the parameters (or some combination of them) of the model) is based on finding the (time) integral of Q(t) according to:

$$\int_0^T Q(t)dt = \int_0^T dt \int_0^t C_a(u)R(t-u)du \quad (4a)$$

Interchanging the order of integration:

$$\int_0^T Q(t)dt = \int_0^T du \int_u^T C_a(u)R(t-u)dt = \quad (4b)$$
$$\int_0^T C_a(u)du \int_u^T R(t-u)dt = \int_0^T C_a(u)du \int_0^{T-u} R(t)dt$$

The time integral $$\int_0^T Q(t)dt$$

is evaluated for the three time intervals
(iii) (i) $0 \leq T \leq t_o$
(iv) (ii) $t_o^* \leq T \leq t_o + W$
(V) $t_o + W \leq T$ For example when the time integral $$\int_0^T Q(t)dt$$

is evaluated for the time interval $0 \leq T \leq t_o$, then $$\int_0^T Q(t)dt = \int_0^T C_a(u)du \int_0^{T-u} R(t)dt$$

for $0 \leq u \leq T \Leftrightarrow 0 \geq -u \geq -T \Leftrightarrow T \geq T-u \geq 0 \Leftrightarrow 0 \leq T-u \leq T \leq t_o$, therefore:

$$\int_0^T Q(t)dt = 0 \quad (5)$$

When the time integral $$\int_0^T Q(t)dt$$

is evaluated for the time interval $t_o \leq T \leq t_o+W$, then setting $T = t_o+a$, where $a \leq W$, the time integral is:

$$\int_0^T Q(t)dt = F\int_0^{t_o+a} C_a(u)du \int_0^{t_o+a-u} R(t)dt$$

$$= F \cdot \left[\int_0^a C_a(u)du + \int_a^{t_o+a} C_a(u)du\right]\left(\int_0^{t_o+a-u} R(t)dt\right)$$

$$= F \cdot \underbrace{\int_0^a C_a(u)du \int_0^{t_o+a-u} R(t)dt}_{A} + F \cdot \int_a^{t_o+a} C_a(u)du \int_0^{t_o+a-u} R(t)dt$$

A: For $0 \leq u \leq a, t_o+a \geq t_o+a-u \geq t_o$ or $t_o+W \geq t_o+a-u \geq t_o$, then:

$$F\int_0^a C_a(u)du \int_0^{t_o+a-u} R(t)dt = F\int_0^a C_a(u)du\left[\int_0^{t_o} R(t)dt + \int_{t_o}^{t_o+a-u} R(t)dt\right]$$

$$= F\int_0^a C_a(u)du \int_{t_o}^{t_o+a-u} R(t)dt = F(a-u)\int_0^a C_a(u)du.$$

B: For $a \leq u \leq a+t_o, t_o \geq t_o+a-u \geq 0$, then $$F * \int_a^{t_o+a} C_a(u)du \int_0^{t_o+a-u} R(t)dt = 0$$

Combining A and B above:

$$\int_0^T Q(t)dt = F * \int_0^a (a-u)C_a(u)du \quad \text{or,} \quad (6a)$$

$$F\left[(T-t_o)\int_0^{T-t_o} C_a(u)du - \int_0^{T-t_o} uC_a(u)du\right] = \int_0^T Q(t)dt$$

When the time integral $$\int_0^T Q(t)dt$$

is evaluated for the time interval $T \geq t_o+W$, then and setting $T = t_o+W+a$, where $a \geq 0$ then $$\int_0^T Q(t)dt = F \cdot \int_0^T C_a(u)du \int_0^{T-u} R(t)dt$$

$$= F * \int_0^{t_o+a+W} C_a(u)du \int_0^{t_o+a+W-u} R(t)dt$$

$$= F\left[\int_0^a C_a(u)du + \int_a^{a+W} C_a(u)du + \int_{a+W}^{t_o+a+W} C_a(u)du \int_0^{t_o+a+W-u} R(t)dt\right]$$

$$= F\underbrace{\int_0^a C_a(u)du \int_0^{t0+a+w-u} R(t)dt}_{C} + F\underbrace{\int_a^{a+W} C_a(u)du \int_0^{t0+a+W-u} R(t)dt}_{D} +$$

$$F\underbrace{\int_{a+W}^{t0+a+W} C_a(u)du \int_0^{t0+a+W-u} R(t)dt}_{E}$$

C: For $0 \leq u \leq a, t_o+a+W \geq t_o+a+W-u \geq t_o+W$, then $$F\int_0^a C_a(u)du \int_0^{t_o+a+W-u} R(t)dt = F\int_0^a C_a(u)du$$

$$\left[\int_0^{t_o} R(t)dt + \int_0^{t_o+W} R(t)dt + \int_{t_o+W}^{t_o+a+W-u} R(t)dt\right]$$

$$= F\int_0^a C_a(u)du\left[W + \int_{t_o+W}^{t_o+a+W-u} R(t)dt\right] =$$

$$FW\int_0^a C_a(u)du + F\int_0^a C_a(u)du \int_{t_o+W}^{t_o+a+W-u} R(t)dt$$

$$= FW\int_0^a C_a(u)du + F\int_0^a C(u)du \int_{t_o+W}^{t_o+a+W-u} Ee^{-k(t-t_o-W)}dt =$$

$$FW\int_0^a C_a(u)du + FE\int_0^a C_a(u)du \int_0^{a-u} e^{-kt}dt$$

$$= FW\int_0^a C_a(u)du - \frac{FE}{k}\int_0^a C_a(u)du[e^{-k(a-u)} - 1]$$

$$= FW\int_0^a C_a(u)du + \frac{FE}{k}\int_0^a C_a(u)du - \underbrace{\frac{FE}{k}\int_0^a C_a(u)e^{-k(a-u)}du}_{F}$$

$$Q(T) = F\int_0^T C_a(u)R(T-u)du = F\int_0^{t_o+a+W} C_a(u)R(t_o+a+W-u)du$$

$F$:

$$= F\int_0^a C_a(u)R(t_o+a+W-u)du + F\int_a^{a+W} C_a(u)R(t_o+a+W-u)du +$$

$$F\int_{a+W}^{t_o+a+W} C_a(u)R(t_o+a+W-u)du$$

$$= FE\int_0^a C_a(u)e^{-k(a-u)}du + F\int_a^{a+W} C_a(u)du$$

Therefore, $\frac{FE}{k}\int_0^a C_a(u)e^{-k(a-u)}du = \frac{Q(T)}{k} - \frac{F}{k}\int_a^{a+W} C_a(u)du$ and $$F\int_0^a C_a(u)du \int_0^{t_o+a+W-u} R(t)dt =$$

$$FW\int_0^a C_a(u)du + \frac{FE}{k}\int_0^a C_a(u)du - \frac{Q(T)}{k} + \frac{F}{k}\int_a^{a+W} C_a(u)du$$

$C$:

D: For $a \leq u \leq a+W, t_o+W-u \geq t_o+a+W-u \geq t_o \Leftrightarrow t_o+W \geq t_o+a+W-u \geq t_o$ $$F\int_a^{a+W} C_a(u)du \int_0^{t_o+a+W-u} R(t)dt =$$

$$F\int_a^{a+W} C_a(u)du \left[\int_0^{t_o} R(t)dt + \int_{t_o}^{t_o+a+W-u} R(t)dt\right]$$

$$= F\int_a^{a+W} C_a(u)du \int_{t_o}^{t_o+a+W-u} R(t)dt = F[a+W-u]\int_a^{a+W} C_a(u)du$$

E: For $a+W \leq u \leq a+W+t_o, t_o \geq t_o+a+W-u \geq 0$ $$F\int_{a+W}^{t_o+a+W} C_a(u)du \int_0^{t_o+a+W-u} R(t)dt = 0$$

Therefore, for $T-t_o+W+a$, where $a \geq 0$:

$$\int_0^T Q(t)dt = FW\int_0^a C_a(u)du + \frac{FE}{k}\int_0^a C_a(u)du - \frac{Q(T)}{k} + \frac{F}{k}\int_a^{a+W} C_a(u)du + F[a+W-u]\int_0^{a+W} C_a(u)du \quad (7a)$$

or, $$QT = Fk\left[W\int_0^{a+W} C_a(u)du + a\int_a^{a+W} C_a(u)du - \int_a^{a+W} uC_a(u)du\right] + F\int_a^{a+W} C_a(u)du + FE\int_0^{a+W} C_a(u)du - k\int_0^T Q(t)dt$$

$$= Fk\left[W\int_0^{T+t_o} C_a(u)du + (T-t_o-W)\int_{T-t_o-W}^{T-t_o} C_a(u)du - \int_{T-t_o-W}^{T-t_o} uC_a(u)du\right] + F\int_{T-t_o-W}^{T-t_o} C_a(u)du + FE\int_0^{T-t_o-W} C_a(u)du - k\int_0^T Q(t)dt \quad (7b)$$

In one embodiment, the time integral $$\int_0^T Q(t)dt$$

for the three time intervals
(i) $0 \leq T \leq t_o$
(ii) $t_o \leq T \leq t_o+W$
(iii) $t_o+W \leq T$
generates the following system of linear equations $$0 = -k\int_0^T Q(t)dt \quad 0 \leq T \leq t_o$$

$$0 = Fk\left[(T-t_o)\int_0^{T-t_o} C_a(u)du - \int_0^{T-t_o} uC_a(u)du\right] - k\int_0^T Q(t)dt \quad t_o \leq T \leq t_o+W$$

$$Q(T) = Fk\left[W\int_0^{T-t_o} C_a(u)du + (T-t_o-W)\int_{T-t_o-W}^{T-t_o} C_a(u)du - \int_{T-t_o-W}^{T-t_o} uC_a(u)du\right] + F\int_{T-t_o-W}^{T-t_o} C_a(u)du + FE\int_0^{T-t_o-W} C_a(u)du - k\int_0^T Q(t)dt \quad T \geq t_o+W$$

involving a plurality of unknowns Fk, F, FE and k, provided that $t_0$ and W are known.

For a set of given $t_0$ and W, a least squares algorithm is used to estimate Fk, F, FE and k subject to the following linear constraints:
Fk $\geq$ 0
F $\geq$ 0
FE $\geq$ 0
k $\geq$ 1
Fk $\geq$ F
F $\geq$ FE The algorithm for estimating $t_0$, W, Fk, F, FE and k includes two main golden section search subroutines. An outer golden section search subroutine searches for $t_0$, an inner golden section search subroutine searches for W with the value of $t_0$, assumed in the outer routine. Within the inner golden section search routine, values of $t_0$ and W are fixed and the optimization of Fk, F, FE and k can proceed with LDP algorithms.

In one embodiment, values of F, E, Ve and k are: F=0.1 ml/min/g, E=0.5, Ve0.25, interstitial space, and k=FE/Ve= O0.2 min−1=12s−1. In another embodiment, values of F, E, $V_e$ and k are: F=0.1 ml/min/g, E=0.25, $V_e$0.25, interstitial space, and k=FE/$V_e$=0.1 min$^{-1}$=6s$^{-1}$.

Although k>=1 is the constraint, after solution, for any k>5s$^{-1}$ assumes that there is no leakage and do not calculate PS, and recalculate blood volume and MTT instead of taking W as MTT and EW as volume. The volume can be taken as the area underneath the flow scaled impulse residue function (F.R(t)), and MTT as the volume divided by the height of the flow scaled impulse residue function.

Discretization of the system of linear equations is performed according to:

Let $\Delta t$ be the time interval, and $t_0=m\Delta t$, W=$n\Delta t$, and T=$i\Delta t$, then:

$$0 = -k\sum_{j=1}^{i} Q(j)\Delta t \quad 0 \leq i \leq m \quad (9)$$

$$0 = Fk\left[(i-m)\Delta t \sum_{j=1}^{i-m} C_a(j)\Delta t - \sum_{j=1}^{i-m} jC_a(j)\Delta t\right] - k\sum_{j=1}^{i} Q(j)\Delta t \quad m \leq i \leq n+m$$

$$Q(T) = Fk\left[W\sum_{j=1}^{i-m} C_a(j)\Delta t + (i-m-n)\Delta t \sum_{j=i-m-n}^{i-m} C_a(j)\Delta t - \sum_{j=i-m-n}^{i-m} C_a(j)\Delta t\right] + F\sum_{j=i-m-n}^{i-m-n} C_a(j)\Delta t + FE\sum_{j=1}^{i-m-n} C_a(j)\Delta t - k\sum_{j=1}^{i} Q(j)\Delta t \quad i \geq n+m$$

The various sums involving the arterial function $C_a(t)$ can be pre-calculated and stored in 2-dimensional arrays AAR and AFM. For example, $$\sum_{j=i-m-n}^{i-m} C_a(j)\Delta t$$

as the [(i−m−n),(i−m)]th element of Area array referred to herein as an arterial area array (AAR). Also, $$\sum_{j=i-m-n}^{i-m} C_a(j)\Delta t$$

as the [(i−m−n),(i−m)]th element of First-moment array referred to herein as an arterial first moment array (AFM). The various sums involving the tissue residue function $Q(t)$ can be pre-calculated and stored in a 1-dimensional array AQ. For example, $$\sum_{j=1}^{i-m} Q(j)\Delta t$$

as the ith element of an array for area of tissue residue function $Q(t)$, (AQ).

A solution for F, E, and k when $t_0$ and W are known can be determined as follows:
Using the arrays: Q, AAR, AFM and AQ, Eq. (9) can be written as Eq. (10):

$$\begin{bmatrix} Q(1)=0 \\ \vdots \\ Q(m)=0 \\ Q(m+1)=0 \\ Q(m+2)=0 \\ \vdots \\ Q(M+n) \\ Q(m+n+1) \\ Q(m+n+2) \\ \vdots \\ Q(m+n+p) \end{bmatrix} = \begin{bmatrix} 0 & 0 & 0 & -AQ(1) \\ \vdots & \vdots & \vdots & \vdots \\ 0 & 0 & 0 & -AQ(m) \\ \Delta t \cdot AAR(1,1) - AFM(1,1) & 0 & 0 & -AQ(m+1) \\ 2\Delta t \cdot AAR(1,2) - AFM(1,2) & 0 & 0 & -AQ(m+2) \\ \vdots & \vdots & \vdots & \vdots \\ n \cdot \Delta t \cdot AAR(1,n) - AFM(1,n) & 0 & 0 & -AQ(m+n) \\ n \cdot \Delta \cdot AAR(1,n+1) + \Delta t \cdot AAR(1,n+1) - AFM(1,n+1) & AAR(1,1) & AAR(1,1) & -AQ(m+n+1) \\ n \cdot \Delta t \cdot AAR(1,n+2) + 2 \cdot \Delta T \cdot AAR(2,n+2) - AFM(2,n+2) & AAR(2,n+2) & AAR(1,2) & -AQ(m+n+2) \\ \vdots & \vdots & \vdots & \vdots \\ n \cdot \Delta t \cdot AAR(1,n+p) + p \cdot \Delta t \cdot AAR(p,n+p) - AFM(p,n+p) & AAR(p,n+p) & AAR(1,p) & -AQ(m+n+p) \end{bmatrix} \begin{bmatrix} Fk \\ F \\ FE \\ k \end{bmatrix}$$

or Q=Ax
and:

$$Q = \begin{bmatrix} Q(1)=0 \\ \vdots \\ Q(m)=0 \\ Q(m+1)=0 \\ Q(m+2)=0 \\ \vdots \\ Q(M+n) \\ Q(m+n+1) \\ Q(m+n+2) \\ \vdots \\ Q(m+n+p) \end{bmatrix} \quad A = \begin{bmatrix} 0 & 0 & 0 & -AQ(1) \\ \vdots & \vdots & \vdots & \vdots \\ 0 & 0 & 0 & -AQ(m) \\ \Delta t \cdot AAR(1,1) - AFM(1,1) & 0 & 0 & -AQ(m+1) \\ 2\Delta t \cdot AAR(1,2) - AFM(1,2) & 0 & 0 & -AQ(m+2) \\ \vdots & \vdots & \vdots & \vdots \\ n \cdot \Delta \cdot \Delta t \cdot AA1,n) - AFM(1,n) & 0 & 0 & -AQ(m+n) \\ n \cdot \Delta \cdot \Delta \cdot AA1,n+1) + \Delta t \cdot AAR(1,n+1) - AFM(1,n+1) & AAR(1,n+1) & AAR(1,1) & -AQ(m+n+1) \\ n \cdot \Delta \cdot \Delta t \cdot AA1,n+2) + 2 \cdot \Delta\Delta T \cdot AAR2,n+2) - AFM(2,n+2) & AAR(2,n+2) & AAR(1,2) & -AQ(m+n+2) \\ \vdots & \vdots & \vdots & \vdots \\ n \cdot \Delta \cdot \Delta t \cdot AA1,n+p) + p \cdot \Delta \cdot \Delta t \cdot AARn+p) - AFM(p,n+p) & AAR(p,n+p) & AAR(1,p) & -AQ(m+n+p) \end{bmatrix} \quad x = \begin{bmatrix} Fk \\ F \\ FE \\ k \end{bmatrix}$$

The constraints are:

$$\begin{bmatrix} 1 & 0 & 0 & 0 \\ 0 & 1 & 0 & 0 \\ 0 & 0 & 1 & 0 \\ 0 & 0 & 0 & 1 \\ 1 & -1 & 0 & 0 \\ 0 & 1 & -1 & 0 \end{bmatrix} \begin{bmatrix} Fk \\ F \\ FE \\ k \end{bmatrix} = \begin{bmatrix} 0 \\ 0 \\ 0 \\ 1 \\ 0 \\ 0 \end{bmatrix} \text{ or, } Gx \geq b \quad (11a)$$

$$G = \begin{bmatrix} 1 & 0 & 0 & 0 \\ 0 & 1 & 0 & 0 \\ 0 & 0 & 1 & 0 \\ 0 & 0 & 0 & 1 \\ 1 & -1 & 0 & 0 \\ 0 & 1 & -1 & 0 \end{bmatrix} \text{ and } b = \begin{bmatrix} 0 \\ 0 \\ 0 \\ 1 \\ 0 \\ 0 \end{bmatrix}$$

Therefore, the solution for the model parameters given $t_0$ and W can be stated as linear least squares problem for x according to q=Ax, subject to the linear inequality constraints $Gx \geq b$ wherein q is a (m+n+p)×1 vector, A is a (m+n+p)×4 matrix, b is a 6×1 vector, and x is a 4×1 vector of the model parameters. In one embodiment, A has a rank of 4, i.e., full column rank and has the following singular value decomposition:

$$A = U \begin{bmatrix} S \\ O \end{bmatrix} V^T,$$

where S is a 4×4 diagonal matrix with its diagonal entries equal to the singular values of A, U and V are orthogonal matrices of dimensions (m+n+p)×(m+n+p) and 4×4 respectively.

The least squares solution, $\hat{x}$, of the least squares problem Q=Ax will minimize $\|Ax-Q\|^2$. Using the singular value decomposition of A, $\|Ax-Q\|^2$ can be simplified as $$\|Ax-Q\|^2 = \left\| U\begin{bmatrix} S \\ 0 \end{bmatrix} V^T x - Q \right\|^2 = U^T U \left\| \begin{bmatrix} S \\ 0 \end{bmatrix} V^T x - U^T Q \right\|^2,$$

since $U^T$ is orthogonal, $$= \left\| \begin{bmatrix} S \\ 0 \end{bmatrix} V^T x - U^T Q \right\|^2 = \left\| \begin{bmatrix} SV^T x \\ 0 \end{bmatrix} - \begin{bmatrix} U_1^T Q \\ U_2^T Q \end{bmatrix} \right\|^2, \text{ and}$$

$$= \left\| \begin{matrix} SV^T x - U_1^T Q \\ -U_2^T Q \end{matrix} \right\|^2 = \|SV^T x - U_1^T Q\|^2 + \|U_2^T Q\|^2$$

Since $\|U_2^T Q\|^2$ is constant, minimizing $\|Ax-Q\|^2$ is equivalent to minimizing $\|SV^T x - U_1^T Q\|^2$. In one embodiment, variable x is changed to z, therefore, $z = SV^T x - U_1^T Q \Leftrightarrow V^T x = S^{-1} z + S^{-1} U_1^T Q$. Minimizing $\|Ax-Q\|^2$ is the same as minimizing $\|z\|^2$. Therefore, the inequality constraint becomes:

$Gx \geq b$
$\Leftrightarrow G((VV^T)x \geq b$
$\Leftrightarrow GV(S^{-1}z + S^{-1}U_1^T Q) \geq b$
$\Leftrightarrow GV(S^{-1}z + S^{-1}U_1^T Q) \geq b$
$\Leftrightarrow GVS^{-1}z \geq b - GVS^{-1}U_1^T Q$ Therefore, minimizing $\|Ax-Q\|^2$ subject to the constraint $GX \geq b$ is equivalent to minimizing $\|z\|^2$ subject to $GVS^{-1}z \geq b - GVS^{-1}U_1^T Q$. In one embodiment, the coefficient matrix of the above system of linear systems will be singular value decomposed (SVD). It can be seen that the coefficient matrix is dependent on Q(t), this means that the SVD of the coefficient matrix has to be repeated for each tissue residue function. The coefficient matrix is N×4 where N is the number of data points of the tissue residue function. The first 3 columns of each coefficient matrix is the same being only dependent on the arterial function. Therefore, SVD of the N×3 matrix can be calculated, and for each tissue residue function, the fourth column is appended according to:

$$\left[ -k \sum_{j=1}^{1} Q(j)\Delta t, k \sum_{j=1}^{2} Q(j)\Delta t, k \sum_{j=1}^{3} Q(j)\Delta t, \cdots, k \sum_{j=1}^{N} Q(j)\Delta t \right]^T.$$

The SVD of the N×4 coeffficient matrix is then calculated from an update of the SVD of the basic N×3 matrix. In one embodiment, the effect of partial volume averaging (PVA) of the arterial curve on the determination of F and V with the deconvolution method can be determined. For example, letting Q(t) be the brain curve of specific mass of contrast in tissue, $C_a(t)$ be the arterial curve of contrast concentration, R(t) be the impulse residue function, F be the blood flow, V be the blood volume, and MTT be the mean transit time. Then, if blood flow is stationary and CT measurement is linear with respect to contrast concentration, by principle of linear superposition then Q(t)=FC$_a$(t)*R(t).

Also, if the arterial curve is underestimated due to partial volume averaging from the finite resolution of CT scanners (~8 lp/cm) then $C_a'(t) = k \cdot C_a(t)$, where $C_a'(t)$ is the arterial curve measured with partial volume averaging (PVA) and k is the multiplicative factor due to PVA, which is less than one. Therefore, $$Q(t) = \frac{F}{k} C_a'(t) * R(t).$$

The deconvolution between Q(t) and $C_a'(t)$ gives $$\frac{F}{k} R(t).$$

The maximum height of $$\frac{F}{k} R(t) \text{ is } \frac{F}{k}$$

and the area underneath $$\frac{F}{k} R(t) \text{ is } \frac{V}{k}.$$

This explains why when a partial volume averaged arterial curve is used in the deconvolution with the brain curve, both F and V are scaled by $$\frac{1}{k} (>1).$$

Note that $$MTT = \frac{F}{V}$$

is not scaled even in this case when the arterial curve is measured with partial volume averaging.

In one embodiment, a correction for partial volume averaging of the arterial curve uses the factor k such that $C_a'(t) = k * C_a(t)$, therefore $$k = \frac{\int_0^\infty C_a'(t) dt}{\int_0^\infty C_a(t) dt}.$$

Note that $C_a'(t)$ is the measured (known) arterial curve i.e. the integral in the numerator can be calculated, while $C_a(t)$ is the true arterial curve which is unknown. If we assume that there exist regions in veins which are free of partial volume averaging, then unlike arterial curves, venous curves can be measured accurately.

For example, let h(t) be the transit time spectrum from artery to veins, therefore $C_v(t) = C_a(t) * h(t)$. Since h(t) is a transit time spectrum, by definition $$\int_0^\infty h(t) dt = 1.$$

Therefore $$\int_0^\infty C_v(t)\,dt = \int_0^\infty C_a(t)\,dt, \text{ and } k = \frac{\int_0^\infty C_a'(t)\,dt}{\int_0^\infty C_v(t)\,dt},$$

where k is expressed in terms of the partial volume averaged arterial curve ($C_a'(t)$) and the venous curve $C_v(t)$. Both of which are known (measured). In one embodiment, $C_a'(t)$ and $C_v(t)$ do not return to baseline during the measurement time, therefore integration to infinity is not desirable since $C_v(t) = C(t)*h(t)$, and therefore, $$C_v(t) = C_a'(t) * \frac{h(t)}{k}.$$

In other words, $$\frac{h(t)}{k}$$

can be obtained by deconvolution between $C_v(t)$ and $C_a'(t)$, for example if $C_{a\,ex}'(t)$ is the extrapolated arterial curve obtained by extrapolation of the trailing slope of $C_a'(t)$ with an exponential function. $C_{a\,ex}'(t)$ returns to baseline very rapidly such that $$\int_o^\infty C_{a,ex}'(t)\,dt$$

can be easily calculated. Since $$\frac{h(t)}{k}$$

and $C_{a\,ex}'(t)$ are both known, their convolution can be calculated as $$C_{v,ex}(t) = C_{a,ex}'(t) * \frac{h(t)}{k}.$$

Similar to $C_{a,ex}'(t)$, $C_{v,ex}(t)$ also returns rapidly to zero baseline and $$\int_0^\infty C_{v,ex}(t)\,dt = \frac{1}{k}\int_0^\infty C_{a,ex}'(t)\,dt,$$

or $$k = \frac{\int_0^\infty C_{a,ex}'(t)\,dt}{\int_0^\infty C_{v,ex}(t)\,dt} = \frac{\int_o^T C_{a,ex}'(t)\,dt}{\int_0^T C_{v,ex}(t)\,dt},$$

where [0,T] is the time interval within which $C_{a,ex}'(t)$ and $C_{v,ex}(t)$ first increase from zero baseline and then decrease back to zero baseline again. Therefore, the time shift between $C_{a,ex}'(t)$ and $C_{v,ex}(t)$ will not affect the calculation of k.

While the invention has been described in terms of various specific embodiments, those skilled in the art will recognize that the invention can be practiced with modification within the spirit and scope of the claims.

What is claimed is:

1. A method for determining tissue type, said method comprising:
   quantitatively determining a tissue blood flow (TBF) by deconvoluting Q(t) and $C_a$(t), where Q(t) is a tissue residue function and represents a curve of specific mass of contrast in tissue, and $C_a$(t) represents an arterial curve of contrast concentration for a tissue having a blood stream containing a contrast without leaking the contrast into an interstitial space of the tissue by solving a matrix equation of Q=Ah for a vector h, and determining a least squares solution for the vector h under an equality constraint, wherein vector h includes a plurality of elements comprising an impulse residue function at different times Q comprises a vector including elements comprising values of a tissue residue function at different times, A comprises a matrix formed by values of the arterial curve of contrast concentration at different times;
   quantitatively determining a tissue blood volume (TBV) by deconvoluting Q(t) and $C_a$(t), quantitatively determining a TBV comprises quantitatively determining a TBV for the tissue by solving the matrix equation of Q=Ah for the vector h, and determining a least squares solution for the vector h under an equality constraint;
   quantitatively determining a tissue mean transit time (TMTT) by deconvoluting Q(t) and $C_a$(t), quantitatively determining a TMTT comprises quantitatively determining a TMTT for the tissue by solving the matrix equation of Q=Ah for the vector h, and determining a least squares solution for the vector h under an equality constraint; and
   determining a tissue type based on the TBF, the TBV, and the TMTT.

2. A method in accordance with claim 1 wherein determining a least squares solution comprises determining a least squares solution for the vector h under a time causality constraint and a minimum transit time constraint.

3. A method in accordance with claim 2 wherein determining a least squares solution further comprises determining a least squares solution for the vector h under a smoothness constraint, a nonnegativity constraint, and a monotonicity constraint, wherein the smoothness constraint forces h to be smoothly varying, and the monotonicity and nonnegativity constraints force h to start at a maximum and then monotonically decreases towards a zero baseline.

4. A method in accordance with claim 1 further comprising quantitatively determining a partial volume averaging scaling factor for the arterial curve of contrast concentration by:
   deconvoluting the measured arterial curve of contrast concentration with a venous curve of contrast concentration to determine a transit time spectrum through a tissue of interest;
   extrapolating the arterial curve; and
   convolving the extrapolated arterial curve with the transit time spectrum to generate an extrapolated venous curve, wherein the partial volume averaging scaling factor is the ratio of an area underneath the extrapolated arterial curve to an area underneath the extrapolated venous curve.

5. A method in accordance with claim 1 wherein the TBF is a cerebral blood flow (CBF), the TBV is a cerebral blood volume (CBV), and the TMTT is a cerebral mean transit time (CMTT), said determining a tissue type based on the TBF, the TBV, and the TMTT comprises determining one of a viable tissue and a non-viable tissue based on the CBF, the CBV, and the CMTT.

6. A method for determining tissue type, said method comprising:

quantitatively determining a tissue blood flow (TBF) by deconvoluting Q(t) and $C_a(t)$, and their combinations thereof, where Q(t) is a tissue residue function and represents a curve of specific mass of contrast in tissue, and $C_a(t)$ represents an arterial curve of contrast concentration for a tissue having a blood stream containing a contrast with leaking the contrast into an interstitial space of the tissue by solving a matrix equation of Q=Ax from the linearization of the tissue residue function for a vector x, wherein vector x includes a plurality of elements comprising TBF, tissue blood volume TBV, tissue mean transit time TMTT, tissue permeability surface area TPS and combinations thereof, Q comprises a vector including elements comprising values of a tissue residue function at different times, A comprises a matrix formed by values of the arterial curve of contrast concentration and tissue residue function at different times and their combinations thereof, quantitatively determining a TBF comprises quantitatively determining a TBF for the tissue by solving the matrix equation of Q=Ax for the vector x, quantitatively determining a TBV comprises quantitatively determining a TBV for the tissue by solving the matrix equation of Q=Ax for the vector x, quantitatively determining a TMTT comprises quantitatively determining a TMTT for the tissue by solving the matrix equation of Q=Ax for the vector x, quantitatively determining a TPS comprises quantitatively determining a TPS for the tissue by solving the matrix equation of Q=Ax for the vector x; and determining a tissue type based on the TBF, TBV, TMTT, and the TPS.

7. A method in accordance with claim 6 further comprising determining a least squares solution for the TBF, the TBV, the TMTT, and the TPS under a nonnegativity constraint that determines a TBV, a TBF, a TMTT and a TPS for the tissue where there is leakage of the contrast from the blood stream into the interstitial space.

8. A method in accordance with claim 6 further comprising quantitatively determining a partial volume averaging scaling factor for the arterial curve of contrast concentration by:

deconvoluting the measured arterial curve of contrast concentration with a venous curve of contrast concentration to determine a transit time spectrum through a tissue of interest;

extrapolating the arterial curve; and convolving the extrapolated arterial curve with the transit time spectrum to generate an extrapolated venous curve, wherein the partial volume averaging scaling factor is the ratio of an area underneath the extrapolated arterial curve to an area underneath the extrapolated venous curve.

9. An imaging system comprising at least one of a computed tomography system and a nuclear magnetic resonance system, said imaging system configured to:

measure Q(t) and $C_a(t)$, where Q(t) is a tissue residue function and represents a curve of specific mass of contrast in tissue, and $C_a(t)$ represents an arterial curve of contrast concentration;

quantitatively determine a tissue blood flow (TBF) for a tissue having a blood stream containing a contrast without leaking the contrast into an interstitial space of the tissue by solving a matrix equation of Q=Ah for a vector h, and determining a least squares solution for the vector h under an equality constraint, wherein vector h includes a plurality of elements comprising an impulse residue function at different times, Q comprises a vector including elements comprising values of a tissue residue function at different times, A comprises a matrix formed by values of the arterial curve of contrast concentration at different times;

quantitatively determine a tissue blood volume (TBV) for the tissue by solving the matrix equation of Q=Ah for the vector h, and determining a least squares solution for the vector h under an equality constraint;

quantitatively determine a TMTT for the tissue by solving the matrix equation of Q=Ah for the vector h, and determining a least squares solution for the vector h under an equality constraint; and determine a tissue type based on the TBF, the TBV, and the TMTT.

10. A system according to claim 9 further configured to determine a least squares solution for the vector h under a time causality constraint and a minimum transit time constraint.

11. A system according to claim 9 further configured to determine a least squares solution for the vector h under a smoothness constraint, a nonnegativity constraint, and a monotonicity constraint, wherein the smoothness constraint forces h to be smoothly varying, and the monotonicity and nonnegativity constraints force h to start at a maximum and then monotonically decreases towards a zero baseline.

12. An imaging system comprising at least one of a computed tomography system and a nuclear magnetic resonance system, said imaging system configured to:

measure Q(t) and $C_a(t)$, where Q(t) is a tissue residue function and represents a curve of specific mass of contrast in tissue, and $C_a(t)$ represents an arterial curve of contrast concentration;

quantitatively determine a tissue blood flow (TBF) for a tissue having a blood stream containing a contrast with leaking the contrast into an interstitial space of the tissue by solving a matrix equation of Q=Ax from the linearization of the tissue residue function for a vector x, wherein vector x includes a plurality of elements comprising TBF, tissue blood volume (TBV), tissue mean transit time (TMTT), tissue permeability surface area product (TPS) and combinations thereof, Q comprises a vector including elements comprising values of a tissue residue function at different times, A comprises a matrix formed by values of the arterial curve of contrast concentration and tissue residue function at different times and combinations thereof;

quantitatively determine a TBV for the tissue by solving the matrix equation of Q=Ax for the vector x;

quantitatively determine a TMTT for the tissue by solving the matrix equation of Q=Ax for the vector x;

quantitatively determine a TPS for the tissue by solving the matrix equation of Q=Ax for the vector x; and determine a tissue type based on the TBF, the TBV, the TMTT, and the TPS.

13. A system according to claim 12 further configured to determine a least squares solution for the TBF, the TBV, the TMTT, and the TPS under a nonnegativity constraint that determines a TBV, a TBF, a TMTT and a TPS for the tissue where there is leakage of the contrast from the blood stream into the interstitial space.

14. A system according to claim 12 wherein the TBF is a cerebral blood flow (CBF), the TBV is a cerebral blood volume (CBV), the TMTT is a cerebral mean transit time (CMTT), the TPS is a cerebral TPS, said system further configured to determine one of a viable tissue and a nonviable tissue based on the CBF, the CBV, the CMTT, and the cerebral TPS.

* * * * *

UNITED STATES PATENT AND TRADEMARK OFFICE
CERTIFICATE OF CORRECTION

| | |
|---|---|
| PATENT NO. | : 6,898,453 B2 |
| APPLICATION NO. | : 10/007341 |
| DATED | : May 24, 2005 |
| INVENTOR(S) | : Lee |

Page 1 of 1

It is certified that error appears in the above-identified patent and that said Letters Patent is hereby corrected as shown below:

In Claim 1, column 26, line 15, delete "times Q comprises" and insert therefor --times, Q comprises--.
In Claim 14, column 28, line 61, delete "claim 12 wherein" and insert therefor --claim 12, wherein--.

Signed and Sealed this

Nineteenth Day of August, 2008

JON W. DUDAS
*Director of the United States Patent and Trademark Office*